US012637496B2

(12) United States Patent
Jung et al.

(10) Patent No.: US 12,637,496 B2
(45) Date of Patent: May 26, 2026

(54) **FLAVIN MONONUCLEOTIDE-BINDING PROTEIN VARIANTS HAVING IMPROVED FLUORESCENCE INTENSITY DERIVED FROM *ARABIDOPSIS THALIANA***

(71) Applicants: KOREA UNIVERSITY RESEARCH AND BUSINESS FOUNDATION, Seoul (KR); KOOKMIN UNIVERSITY INDUSTRY ACADEMY COOPERATION FOUNDATION, Seoul (KR)

(72) Inventors: Sang Taek Jung, Gyeonggi-do (KR); Sang Hwan Ko, Seoul (KR); Bora Hwang, Gyeonggi-do (KR); Jung-Hyun Na, Seoul (KR)

(73) Assignees: KOREA UNIVERSITY RESEARCH AND BUSINESS FOUNDATION, Seoul (KR); KOOKMIN UNIVERSITY INDUSTRY ACADEMY COOPERATION FOUNDATION, Seoul (KR)

( * ) Notice: Subject to any disclaimer, the term of this patent is extended or adjusted under 35 U.S.C. 154(b) by 1162 days.

(21) Appl. No.: 17/629,016

(22) PCT Filed: Sep. 29, 2020

(86) PCT No.: PCT/KR2020/013355
§ 371 (c)(1),
(2) Date: Jan. 21, 2022

(87) PCT Pub. No.: WO2021/066528
PCT Pub. Date: Apr. 8, 2021

(65) Prior Publication Data
US 2022/0267387 A1 Aug. 25, 2022

(30) Foreign Application Priority Data
Sep. 30, 2019 (KR) ........................ 10-2019-0120443

(51) Int. Cl.
*C07K 14/415* (2006.01)
(52) U.S. Cl.
CPC .................................. *C07K 14/415* (2013.01)
(58) Field of Classification Search
CPC .... C07K 14/415; C07K 2319/60; C12N 9/12; C12Y 207/11001
See application file for complete search history.

(56) References Cited

U.S. PATENT DOCUMENTS

2010/0304435 A1 12/2010 Eggert
2021/0121582 A1 4/2021 Krishnamani

FOREIGN PATENT DOCUMENTS

CN 105420203 3/2016
KR 101833896 3/2018

OTHER PUBLICATIONS

Davos et al., Proteins: Structure, Function and Genetics, 2000, vol. 41: 98-107.*
Kwiatkowski et al., Biochemistry 38:11643-11650, 1999.*
Kisselev L., Structure, 2002, vol. 10: 8-9.*
Wristlock et al., Quarterly Reviews of Biophysics 2003, vol. 36 (3): 307-340.*
Christie, J.M., et al., "Structural Tuning of the Fluorescent Protein iLOV for Improved Photostability," The Journal of Biological Chemistry, Jun. 22, 2012, vol. 287, No. 26, pp. 22295-22304.
Wingen, M., et al., "The photophysics of LOV-based fluorescent proteins—new tools for cell biology," Photochem. Photobiol. Sci., 2014, 13, 875.
Buckley, A.M., et al., "LOV-based reporters for fluorescence imaging," Current Opinion in Chemical Biology, 2015, 27:39-45.
Shu, X., et al., "A Genetically Encoded Tag for Correlated Light and Electron Microscopy of Intact Cells, Tissues, and Organisms," PLoS Biology, Apr. 2011, vol. 9, Issue 4, e1001041.
Ko, S., et al., "Engineered arabidopsis blue light receptor LOV domain variants with improved quantum yield, brightness, and thermostability", J. Agric. Food Chem. 2019, 67, 12037-12043.
Higgins, S.A., et al., "Rapid and Programmable Protein Mutagenesis Using Plasmid Recombineering," ACS Synth. Biol. 2017, 6, 1825-1833.
Mukherjee, A., et al., "Engineering and Characterization of New LOV-Based Fluorescent Proteins from Chlamydomonas reinhardtii and Vaucheria frigida," ACS Synth. Biol., 2015, vol. 4, No. 4, pp. 371-377.
Khrenova, M.G., "Mutants of the Flavoprotein iLOV as Prospective Red-Shifted Fluorescent Markers," J. Phys. Chem. B., 2017, vol. 121, No. 43, pp. 10018-10025.

* cited by examiner

*Primary Examiner* — Tekchand Saidha
*Assistant Examiner* — Mohammad Y Meah
(74) *Attorney, Agent, or Firm* — DUANE MORRIS LLP; Gregory M. Lefkowitz; Brandon A. Chan

(57) ABSTRACT

The present invention relates to flavoprotein improved LOV (iLOV) variants that exhibit enhanced fluorescence intensity compared to iLOV. The present invention also relates to a method for screening any of the iLOV variants. The iLOV variants of the present invention are useful in determining whether target proteins are expressed, irrespective of the presence of oxygen, and isolating and purifying the expressed target proteins due to their enhanced fluorescence intensity and quantum yield compared to existing LOV or iLOV proteins.

2 Claims, 9 Drawing Sheets
Specification includes a Sequence Listing.

| Mutation site | |
|---|---|
| SH3 | F5Y, S8T, S23G, C40A, I66T, K79E, M89V, D91N, L104Q |
| BR1 | F5Y, S8T, S23G, E29G, C40A, I66T K78R, F84L, M89V, H109R |

| Name | Quantum Yield | Brightness |
|---|---|---|
| iLOV | 0.37 | 4625 |
| SH3 | 0.40 | 5000 |
| BR1 | 0.45 | 5625 |

SEQUENCE LISTING

```
<160> NUMBER OF SEQ ID NOS: 6

<210> SEQ ID NO 1
<211> LENGTH: 110
<212> TYPE: PRT
<213> ORGANISM: Arabidopsis thaliana

<400> SEQUENCE: 1

Ile Glu Lys Asn Phe Val Ile Ser Asp Pro Arg Leu Pro Asp Asn Pro
1               5                   10                  15

Ile Ile Phe Ala Ser Asp Ser Phe Leu Glu Leu Thr Glu Tyr Ser Arg
            20                  25                  30

Glu Glu Ile Leu Gly Arg Asn Cys Arg Phe Leu Gln Gly Pro Glu Thr
        35                  40                  45

Asp Gln Ala Thr Val Gln Lys Ile Arg Asp Ala Ile Arg Asp Gln Arg
    50                  55                  60

Glu Ile Thr Val Gln Leu Ile Asn Tyr Thr Lys Ser Gly Lys Lys Phe
65                  70                  75                  80

Trp Asn Leu Phe His Leu Gln Pro Met Arg Asp Gln Lys Gly Glu Leu
                85                  90                  95

Gln Tyr Phe Ile Gly Val Gln Leu Asp Gly Ser Asp His Val
            100                 105                 110

<210> SEQ ID NO 2
<211> LENGTH: 110
<212> TYPE: PRT
<213> ORGANISM: Artificial Sequence
<220> FEATURE:
<223> OTHER INFORMATION: iLOV
```

<400> SEQUENCE: 2

```
Ile Glu Lys Asn Phe Val Ile Thr Asp Pro Arg Leu Pro Asp Asn Pro
1               5                   10                  15

Ile Ile Phe Ala Ser Asp Gly Phe Leu Glu Leu Thr Glu Tyr Ser Arg
            20                  25                  30

Glu Glu Ile Leu Gly Arg Asn Ala Arg Phe Leu Gln Gly Pro Glu Thr
        35                  40                  45

Asp Gln Ala Thr Val Gln Lys Ile Arg Asp Ala Ile Arg Asp Gln Arg
    50                  55                  60

Glu Thr Thr Val Gln Leu Ile Asn Tyr Thr Lys Ser Gly Lys Lys Phe
65                  70                  75                  80

Trp Asn Leu Leu His Leu Gln Pro Val Arg Asp Gln Lys Gly Glu Leu
                85                  90                  95

Gln Tyr Phe Ile Gly Val Gln Leu Asp Gly Ser Asp His Val
                100                 105                 110
```

<210> SEQ ID NO 3
<211> LENGTH: 110
<212> TYPE: PRT
<213> ORGANISM: Artificial Sequence
<220> FEATURE:
<223> OTHER INFORMATION: SH3

<400> SEQUENCE: 3

```
Ile Glu Lys Asn Tyr Val Ile Thr Asp Pro Arg Leu Pro Asp Asn Pro
1               5                   10                  15

Ile Ile Phe Ala Ser Asp Gly Phe Leu Glu Leu Thr Glu Tyr Ser Arg
            20                  25                  30

Glu Glu Ile Leu Gly Arg Asn Ala Arg Phe Leu Gln Gly Pro Glu Thr
        35                  40                  45

Asp Gln Ala Thr Val Gln Lys Ile Arg Asp Ala Ile Arg Asp Gln Arg
    50                  55                  60

Glu Thr Thr Val Gln Leu Ile Asn Tyr Thr Lys Ser Gly Lys Glu Phe
65                  70                  75                  80

Trp Asn Leu Phe His Leu Gln Pro Val Arg Asn Gln Lys Gly Glu Leu
                85                  90                  95

Gln Tyr Phe Ile Gly Val Gln Gln Asp Gly Ser Asp His Val
                100                 105                 110
```

<210> SEQ ID NO 4
<211> LENGTH: 110
<212> TYPE: PRT
<213> ORGANISM: Artificial Sequence
<220> FEATURE:
<223> OTHER INFORMATION: BR1

<400> SEQUENCE: 4

```
Ile Glu Lys Asn Tyr Val Ile Thr Asp Pro Arg Leu Pro Asp Asn Pro
1               5                   10                  15

Ile Ile Phe Ala Ser Asp Gly Phe Leu Glu Leu Thr Gly Tyr Ser Arg
            20                  25                  30

Glu Glu Ile Leu Gly Arg Asn Ala Arg Phe Leu Gln Gly Pro Glu Thr
        35                  40                  45

Asp Gln Ala Thr Val Gln Lys Ile Arg Asp Ala Ile Arg Asp Gln Arg
    50                  55                  60

Glu Thr Thr Val Gln Leu Ile Asn Tyr Thr Lys Ser Gly Arg Lys Phe
65                  70                  75                  80
```

-continued

```
Trp Asn Leu Leu His Leu Gln Pro Val Arg Asp Gln Lys Gly Glu Leu
                85                  90                  95

Gln Tyr Phe Ile Gly Val Gln Leu Asp Gly Ser Asp Arg Val
            100                 105                 110

<210> SEQ ID NO 5
<211> LENGTH: 24
<212> TYPE: DNA
<213> ORGANISM: Artificial Sequence
<220> FEATURE:
<223> OTHER INFORMATION: Error prone PCR primer (forward)

<400> SEQUENCE: 5
catcaccatc accatcacgg atcc                                          24

<210> SEQ ID NO 6
<211> LENGTH: 29
<212> TYPE: DNA
<213> ORGANISM: Artificial Sequence
<220> FEATURE:
<223> OTHER INFORMATION: Error prone PCR primer (reverse)

<400> SEQUENCE: 6
aagcttaatt agctgagctt ggactcctg                                     29
```

FLAVIN MONONUCLEOTIDE-BINDING PROTEIN VARIANTS HAVING IMPROVED FLUORESCENCE INTENSITY DERIVED FROM *ARABIDOPSIS THALIANA*

CROSS-REFERENCE TO RELATED APPLICATIONS

This application is a § 371 national stage entry of International Application No. PCT/KR2020/013355, filed on Sep. 29, 2020, which claims priority to Korean Patent Application No. 10-2019-0120443, filed on Sep. 30, 2019, the entire contents of which are incorporated herein by reference.

SEQUENCE LISTING

The instant application contains a Sequence Listing, which has been submitted electronically in ASCII format and is hereby incorporated by reference in its entirety. Said ASCII text file, created on Feb. 23, 2022, is named G1035-21801_SequenceListing, and is 4,609 bytes in size.

TECHNICAL FIELD

The present invention relates to flavin mononucleotide-binding fluorescent protein variants with improved fluorescence intensity, and more specifically to the discovery of fluorescent protein variants derived from Arabidopsis thaliana.

BACKGROUND ART

Fluorescent proteins are reporters that can be encoded by genes for bioscience, medical, and pharmaceutical research and have been widely applied to various research fields. Fluorescent proteins are particularly useful in real-time analysis of protein expression, activity, and secretion in cells, animal, and plants. Fluorescent proteins are proteins that are activated by light of a specific wavelength and emit light of a different wavelength when they fall to a lower energy level. Representative fluorescent proteins are, for example, green fluorescent proteins (GFPs) found in marine jellyfish. Green fluorescent proteins have been used as essential tools in bioscience research. The 2008 Nobel Prize was awarded for the discovery of green fluorescent proteins.

The binding of a GFP-producing gene to a protein gene enables tracking and observation of gene expression in cells or tissues based on GFP fluorescence. When a green fluorescent protein gene is inserted into a specific protein gene and injected into cells of an experimental organism, tumor size or location can be tracked over time, enabling visual observation of tumor by illumination with blue light without the need to dissect the organism.

In pharmaceutical protein research, the insertion of a green fluorescent protein gene fused to a target protein gene into an animal makes it to determine whether the target protein is inserted through the green fluorescent protein.

Bioscience studies using GFP gene binding, including neural circuit analysis, cell membrane investigation, and viral infection mechanisms, have also been actively conducted. The development of GFP-incorporated live fluorescent animals has also been reported.

Most of the currently used fluorescent proteins, including GFPs, require the presence of oxygen to form chromophores capable of emitting fluorescence. This limitation makes it difficult to use fluorescent proteins in oxygen-deficient intracellular environments, in oxygen-free environments where anaerobic bacteria sustain their lives, and environments where are deficient in oxygen due to excessive growth of cells.

Meanwhile, flavin-based fluorescent proteins (FbFPs) have been discovered that can be used as fluorescent reporters in bioscience, medical, and pharmaceutical applications irrespective of whether oxygen is present or lacking. However, the use of these flavin-based fluorescent proteins (FbFPs) is limited due to their low fluorescence intensity.

The description of the Background Art is merely provided for better understanding the background of the invention and should not be taken as corresponding to the prior art already known to those skilled in the art.

DETAILED DESCRIPTION OF THE INVENTION

Problems to be Solved by the Invention

The present inventors have earnestly and intensively conducted research to discover flavin-based fluorescent proteins (FbFPs) that can be widely used in bioscience, medical, and pharmaceutical applications irrespective of whether oxygen is present or lacking. As a result, the present inventors have found that when one or more amino acids in the sequence of iLOV, a variant of LOV derived from *Arabidopsis thaliana*, are replaced by other optimal amino acids, the resulting iLOV variants exhibit greatly improved fluorescence intensity compared to the LOV or iLOV protein. The present invention has been accomplished based on this finding.

Accordingly, one object of the present invention is to provide flavoprotein improved LOV (iLOV) variants that exhibit enhanced fluorescence intensity compared to iLOV.

A further object of the present invention is to provide a nucleic acid molecule encoding any of the iLOV variants described herein.

Another object of the present invention is to provide a vector including the nucleic acid molecule.

Another object of the present invention is to provide a host cell including the vector.

Another object of the present invention is to provide a fluorescent composition including the iLOV variant, nucleic acid molecule or vector.

Another object of the present invention is to provide a method for analyzing the expression of a target protein including expressing the vector.

Another object of the present invention is to provide a method for isolating and purifying a target protein including expressing the vector to produce the target protein and isolating the target protein.

Another object of the present invention is to provide a method for producing the iLOV variant.

Still another object of the present invention is to provide a method for screening the iLOV variant.

Other objects and advantages of the invention become more apparent from the following detailed description, claims, and drawings.

Means for Solving the Problems

One aspect of the present invention provides a flavoprotein improved LOV (iLOV) variant that exhibits enhanced fluorescence intensity compared to iLOV.

The present inventors have earnestly and intensively conducted research to discover flavin-based fluorescent proteins (FbFPs) that can be widely used in bioscience, medical, and pharmaceutical applications irrespective of whether oxygen is present or lacking. As a result, the present inventors have found that when one or more amino acids in the sequence of iLOV, a variant of LOV derived from *Arabidopsis thaliana*, are replaced by other amino acids, the resulting optimized iLOV variants exhibit greatly improved fluorescence intensity compared to the LOV or iLOV protein.

As used herein, the term "LOV" or "LOV protein" refers to a sensor domain in higher plants, microalgae, fungi, and bacteria to sense environmental conditions. LOV is an abbreviation for light-oxygen-voltage. In the present invention, the LOV protein is preferably a flavin-based fluorescent protein (FbFP) derived from *Arabidopsis thaliana*. More preferably, the LOV protein includes the sequence set forth in SEQ ID NO: 1.

As used herein, the term "iLOV", "iLOV protein" or "flavoprotein improved LOV" refers to a variant of the LOV protein. The iLOV protein is preferably obtained by substituting the amino acids at positions 8, 23, 40, 66, 84, and 89 in the sequence set forth in SEQ ID NO: 1 with other amino acids. More preferably, the iLOV protein includes the sequence set forth in SEQ ID NO: 2.

According to a preferred embodiment of the present invention, the iLOV variant includes a portion of the amino acid sequence of the iLOV (SEQ ID NO: 2) and a substitution of the phenylalanine (F) at position 5 in the amino acid sequence of the iLOV (SEQ ID NO: 2) to tyrosine (Y).

According to a preferred embodiment of the present invention, the iLOV variant includes a substitution of the phenylalanine (F) at position 5 in the amino acid sequence of the iLOV (SEQ ID NO: 2) to tyrosine (Y) and further includes substitutions of the lysine (K), leucine (L), aspartate (D), and leucine (L) at positions 79, 84, 91, and 104 in the amino acid sequence of the iLOV (SEQ ID NO: 2) to glutamate (E), phenylalanine (F), asparagine (N), and glutamine (Q), respectively.

According to a preferred embodiment of the present invention, the iLOV variant includes a substitution of the phenylalanine (F) at position 5 in the amino acid sequence of the iLOV (SEQ ID NO: 2) to tyrosine (Y) and further includes substitutions of the glutamate (E), lysine (K), and histidine (H) at positions 29, 78, and 109 in the amino acid sequence of the iLOV (SEQ ID NO: 2) to glycine (G), arginine (R), and arginine (R), respectively.

According to a preferred embodiment of the present invention, the iLOV variant includes the amino acid sequence set forth in SEQ ID NO: 3 or 4.

The fluorescence intensity of the iLOV variant according to the present invention is increased by at least 10%, preferably at least 20%, more preferably at least 30%, even more preferably at least 40%, most preferably at least 50%, compared to that of iLOV, a variant of LOV derived from *Arabidopsis thaliana*.

In the Examples section that follows, the inventive iLOV variants exhibited 93% to 277% increases in fluorescence intensity compared to the iLOV protein (FIG. 4).

The iLOV variant of the present invention also exhibits enhanced quantum yield compared to the LOV or iLOV protein.

Quantum yield is defined as the ratio of the number of photons or photoelectrons emitted to the number of photons absorbed upon absorption of light and subsequent emission of photons or photoelectrons. That is, a higher quantum yield indicates a higher conversion of absorbed photons into re-emitted photons. Consequently, a protein with a high quantum yield indicates a bright fluorescence protein. A fluorescent protein with a high quantum yield can be measured to be relatively highly fluorescent even when used in a small amount, which leads to increased sensitivity.

The quantum yield of the iLOV variant according to the present invention is increased by at least 4%, preferably at least 5%, more preferably at least 6%, even more preferably at least 7%, most preferably at least 8%, compared to that of LOV derived from *Arabidopsis thaliana* or iLOV, a variant of LOV.

In the Examples section that follows, the inventive iLOV variants exhibited 8% to 22% increases in quantum yield (FIG. 7).

The iLOV variant of the present invention exhibits enhanced thermal stability compared to the LOV or iLOV protein.

In the Examples section that follows, the inventive iLOV variants showed improved thermostability even at a highly elevated temperature of 45° C. (FIG. 8). Due to this advantage, the iLOV variant of the present invention can be utilized even under high temperature conditions.

A further aspect of the present invention provides a nucleic acid molecule encoding the iLOV variant, a vector including the nucleic acid molecule or a host cell including the vector.

The nucleic acid molecule of the present invention may be an isolated or recombinant one. Examples of such nucleic acid molecules include single- and double-stranded DNA and RNA and their corresponding complementary sequences. The isolated nucleic acid may be isolated from a naturally occurring source. In this case, the isolated nucleic acid is separated from the peripheral gene sequence present in the genome of a subject from which the nucleic acid is to be isolated.

The isolated nucleic acid may be a nucleic acid, for example, a PCR product, a cDNA molecule or an oligonucleotide, that is enzymatically or chemically synthesized from a template. In this case, the nucleic acid produced from this procedure can be understood as the isolated nucleic acid molecule. The isolated nucleic acid molecule represents a nucleic acid molecule in the form of a separate fragment or as a component of a larger nucleic acid construct. A nucleic acid is "operably linked" when arranged in a functional relationship with another nucleic acid sequence. For example, the DNA of a presequence or secretory leader is operably linked to the DNA of the polypeptide when expressed as a preprotein, which is a presecretory polypeptide. A promoter or an enhancer affecting the transcription of the polypeptide sequence is operably linked to a coding sequence or a ribosome-binding site is operably linked to a coding sequence when it is arranged such that translation is promoted. Generally, the term "operably linked" means that DNA sequences to be linked are located adjacent to each other. In the case of secretory leaders, the term "operably linked" means that the secretory leaders are present adjacent to each other in the same leading frame. However, an enhancer needs not be contiguous. The linkage is performed by ligation at a convenient restriction enzyme site. In the case where this site does not exist, a synthetic oligonucleotide adaptor or a linker is used according to a suitable method known in the art.

As used herein, the term "vector" refers to a carrier into which a nucleic acid sequence can be inserted for introduction into a cell where it can be replicated. A nucleic acid sequence may be "exogenous," or "heterologous". Examples of suitable vectors include, but are not limited to, plasmids, cosmids, and viruses (e.g., bacteriophages and AAVs). Those skilled in the art can construct such vectors through standard recombinant techniques (Maniatis et al., *Molecular Cloning*, A Laboratory Manual, Cold Spring Harbor Press, Cold Spring Harbor, N.Y., 1988; and Ausubel et al., In: *Current Protocols in Molecular Biology*, John, Wiley & Sons, Inc, N.Y., 1994, etc.).

As used herein, the term "expression vector" refers to a vector containing a nucleic acid sequence coding for at least part of a gene product capable of being transcribed. In some cases, RNA molecules are then translated into a protein, polypeptide, or peptide. Expression vectors can contain a variety of regulatory sequences. In addition to regulatory sequences that govern transcription and translation, vectors and expression vectors may contain nucleic acid sequences that serve other functions as well.

According to a preferred embodiment of the present invention, the vector includes the nucleic acid molecule as a reporter gene and further includes a target protein to be expressed.

As used herein, the term "target protein" refers to a protein that is intended to be identified or produced using an appropriate host cell.

When the nucleic acid molecule of the present invention is used as a reporter gene, whether the target protein is expressed can be analyzed based on fluorescence, enabling analysis of the target protein expression. In addition, the use of the nucleic acid molecule as a reporter gene facilitates isolation and purification of the target protein after production.

As used herein, the term "host cell" refers to any transgenic organism that is capable of replicating the vector or expressing the gene encoded by the vector. Suitable organisms include eukaryotes and prokaryotes. The host cell may be transfected or transformed by the vector. The transfection or transformation refers to a process for transferring or introducing the exogenous nucleic acid molecule into the host cell.

The host cell of the present invention is preferably a bacterial, yeast or mammalian cell (for example, CHO cell, HeLa cell, HEK293 cell, BHK cell, COS7 cell, COPS cell, A549 cell, NIH3T3 cell, MDCK cell or WI38 cell), but is not limited thereto.

Another aspect of the present invention provides a fluorescent composition including the iLOV variant, nucleic acid molecule or vector.

The fluorescent composition may be prepared in a kit for determining whether the target protein is expressed, isolating and purifying the expressed target protein or imaging specific tissues, cells or molecules.

Another aspect of the present invention provides a method for analyzing the expression of a target protein including expressing the vector.

Another aspect of the present invention provides a method for isolating and purifying a target protein including expressing the vector to produce the target protein and isolating the target protein.

As described above, the use of the nucleic acid molecule according to the present invention as a reporter gene enables a determination as to whether the target protein is expressed and isolation and purification of the target protein after expression. In addition, binding or fusion of the iLOV variant according to the present invention to another protein or molecule enables location and quantification of the protein or molecule based on fluorescence.

Another aspect of the present invention provides a method for producing the iLOV variant including a) culturing a host cell including a vector including a nucleic acid molecule encoding the iLOV variant and b) recovering the iLOV variant expressed by the host cell.

Yet another aspect of the present invention provides a method for screening the iLOV variant including a) randomly introducing additional point mutations into the iLOV variant or a nucleic acid molecule coding therefor and constructing a library of the point-mutated iLOV variants or the nucleic acid molecules coding therefor and b) selecting the iLOV variant or nucleic acid molecule coding therefor with enhanced fluorescence intensity compared to the iLOV protein including the sequence set forth in SEQ ID NO: 2 from the library.

The screening method of the present invention may use fluorescence activated cell sorting (FACS) or flow cytometry. Instruments for flow cytometry are known to those skilled in the art and examples thereof include FACSAria, FACS Star Plus, FACScan and FACSort (Becton Dickinson, Foster City, CA), Epics C (Coulter Epics Division, Hialeah, FL), MOFLO (Cytomation, Colorado Springs, Colo.), and MOFLO-XDP (Beckman Coulter, Indianapolis, IN). Generally, flow cytometry involves the separation of cells or other particles in a liquid sample. A typical purpose of flow cytometry is to analyze the separated particles for their one or more properties (e.g., the presence of labeled ligands or other molecules). Particles pass one by one through a sensor and are sorted based on size, refraction, light scattering, opacity, illuminance, shape, fluorescence, and the like.

Effects of the Invention

The features and advantages of the present invention are summarized as follows:

(i) The present invention provides an iLOV variant with enhanced fluorescence intensity compared to flavoprotein improved LOV (iLOV);

(ii) The present invention also provides a method for screening the iLOV variant; and (iii) The iLOV variant of the present invention is useful in determining whether a target protein is expressed, irrespective of the presence of oxygen, and isolating and purifying the expressed target protein due to its enhanced fluorescence intensity and quantum yield compared to existing LOV or iLOV proteins.

MODE FOR CARRYING OUT THE INVENTION

The present invention will be more specifically explained with reference to the following examples. It will be evident to those skilled in the art that the scope of the present invention is not limited by these examples according to the gist of the present invention.

EXAMPLES

<Example 1> Construction of iLOV Variant Libraries

*Arabidopsis thaliana*-derived FMN-based fluorescent protein (iLOV) was transferred to PQE-80 vector (Qiagen) using BamHI and HindIII (New England Biolab) restriction enzyme sites to construct a plasmid for iLOV expression. With this plasmid as a template, mutations were introduced using an error-prone PCR technique. Primers for error-prone PCR were as follows: 5'-CATCACCATCACCATCACG-GATCC-3', 5'-AAGCTTAATTAGCT-GAGCTTGGACTCCTG-3'. Library inserts were produced whose error rate was adjusted not to exceed 0.5%. The library inserts were digested with BamHI and HindIII (New England Biolab) restriction enzymes, ligated into the PQE-80L vector digested with the same restriction enzymes, and transformed into *Escherichia coli* Jude1 ((F' [Tn10(Tet[1]) proAB$^+$lacl$^q$Δ(lacZ)M15] mcrA Δ(mrr-hsdRMS-mcrBC) f80dlacZΔM15 ΔlacX74 deoR recA1 araD139 Δ(ara leu) 7697 galU galKrpsLendA1nupG) to generate a large iLOV variant library. A secondary library was constructed using primarily sorted variants.

Figure 1:
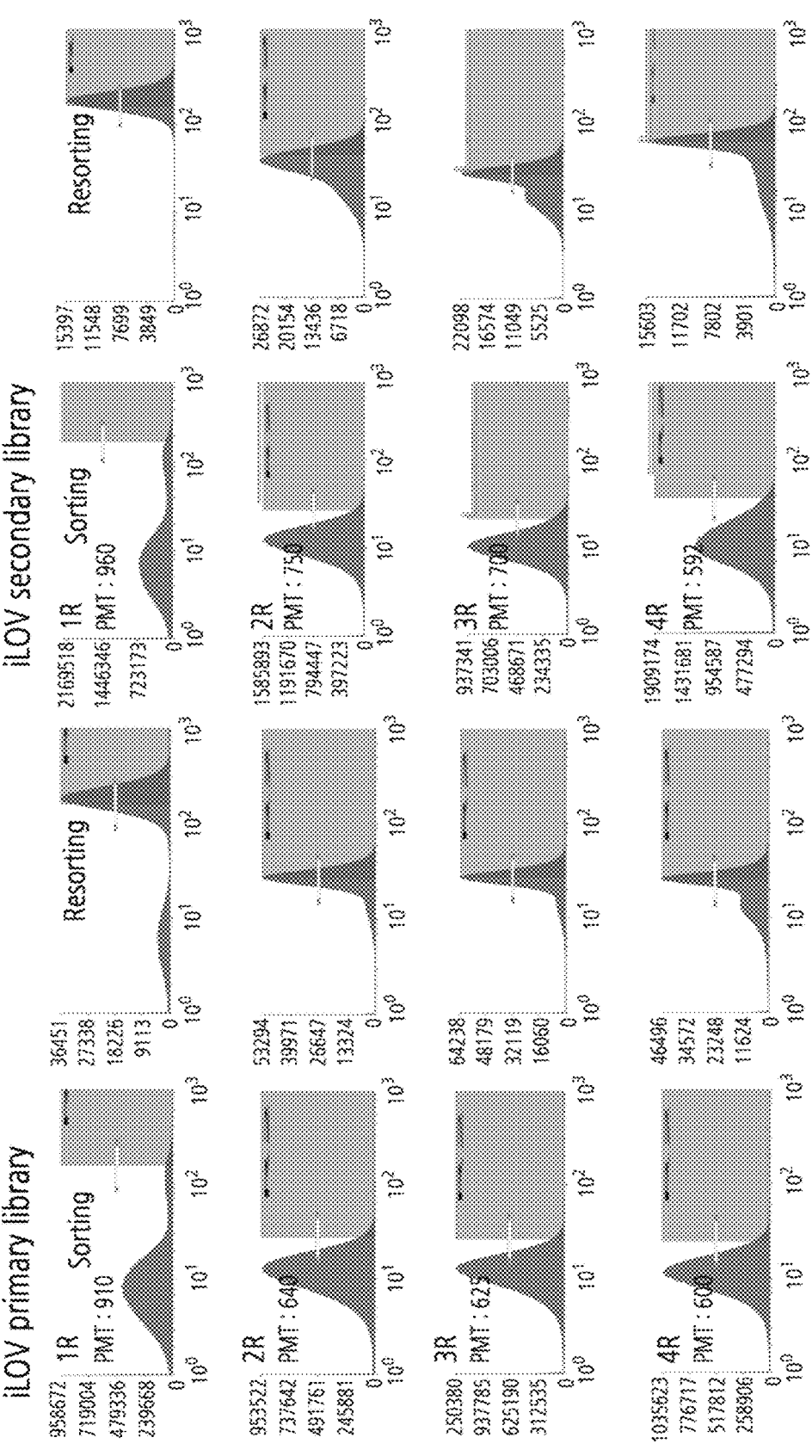
FIG. 1 shows a sorting process using iLOV primary and secondary libraries.

<Example 2> Searching Against the iLOV Variant Libraries Using Bacterial Culture and Flow Cytometry In this example, a search was conducted against the established iLOV variant libraries. First, 1 ml of variant library cells transformed into *Escherichia coli* Jude1 cells were cultured in terrific broth (TB) medium supplemented with 2% (w/v) glucose and ampicillin (40 μg/mL) as an antibiotic at 37° C. for 4 h at 250 rpm shaking. After shaking culture, the library cells were inoculated into TB medium in a ratio of 1:100 and cultured with shaking at 250 rpm and 37° C. until an OD$_{600}$ of 0.5 was reached. Thereafter, culture was further performed at 25° C. for 20 min for cooling and 1 mM isopropyl-1-thio-β-D-galactopyranoside (IPTG) was added to induce expression. After completion of the culture, cells were collected and washed twice with PBS. Sorting was performed by flow cytometry (S3 sortor (Bio-rad)) to recover 2% of the cells with highest fluorescence intensity, which were resorted to improve purity. The resorted sample was immediately inoculated into TB+2% (w/v) glucose supplemented with ampicillin (40 μg/mL), followed by culture overnight. On the next day, cells were inoculated into TB medium supplemented with ampicillin (40 μg/mL) in a ratio of 1:100 and cultured for the next round of flow cytometric screening, where highly fluorescent cells were sorted. 4 rounds of sorting and resorting were performed for each library in the same manner as described above (FIG. 1). As the round progressed, the sensitivity of the detector of the flow cytometer was lowered for higher fluorescence intensity measurements. A secondary library was established based on SH3 sorted from the primary library in the same manner as described above. Thereafter, 4 rounds of sorting and resorting were performed (FIG. 1).

<Example 3> Selection of iLOV Variants with Enhanced Fluorescence Intensity

Figure 2:
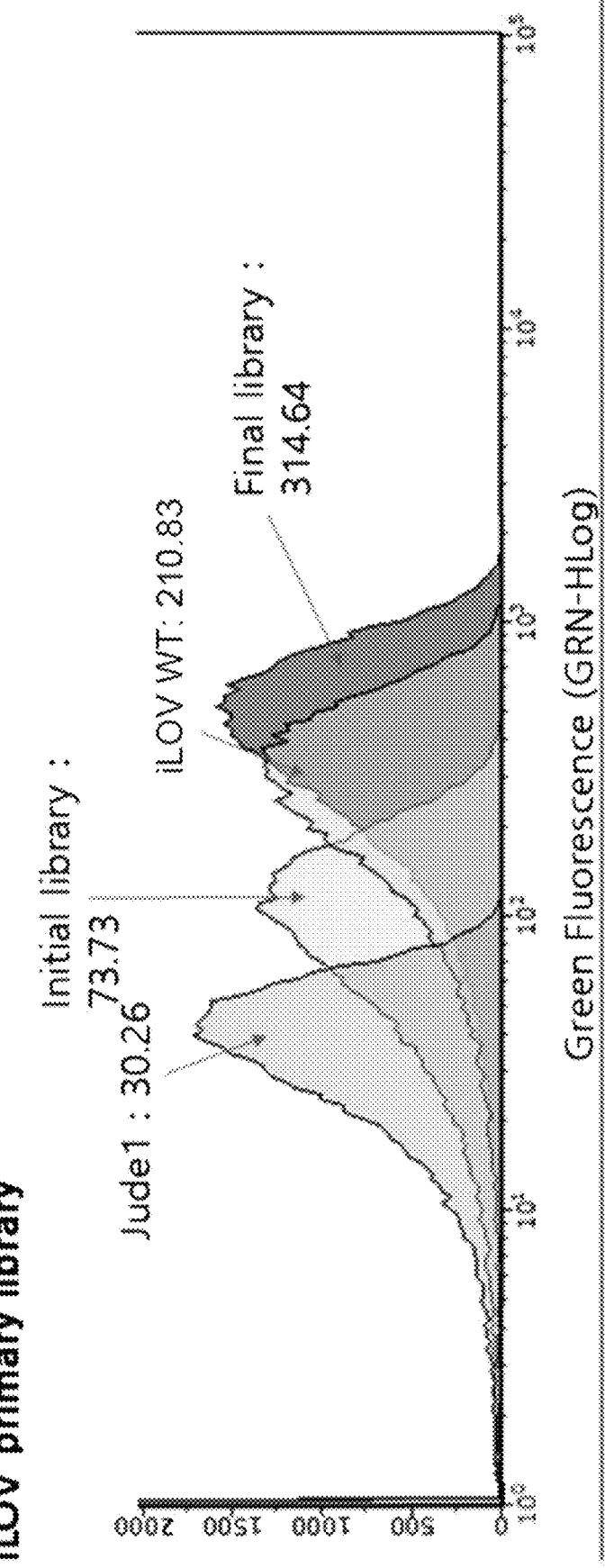
FIG. 2 shows an enrichment test for resulting libraries after iLOV primary screening.
Figure 3:
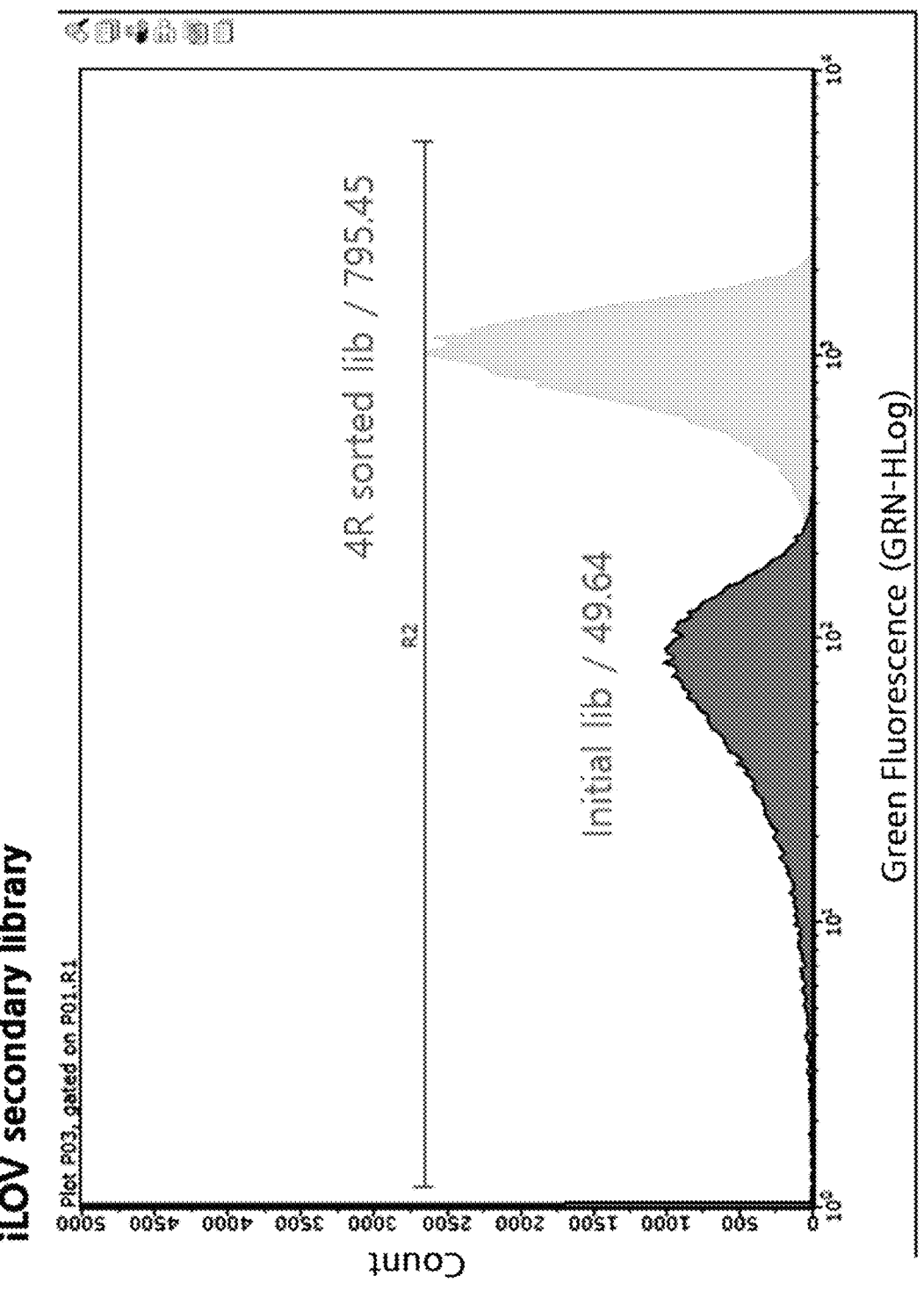
FIG. 3 shows an enrichment test for resulting libraries after iLOV secondary screening.
Figures 4, 5:
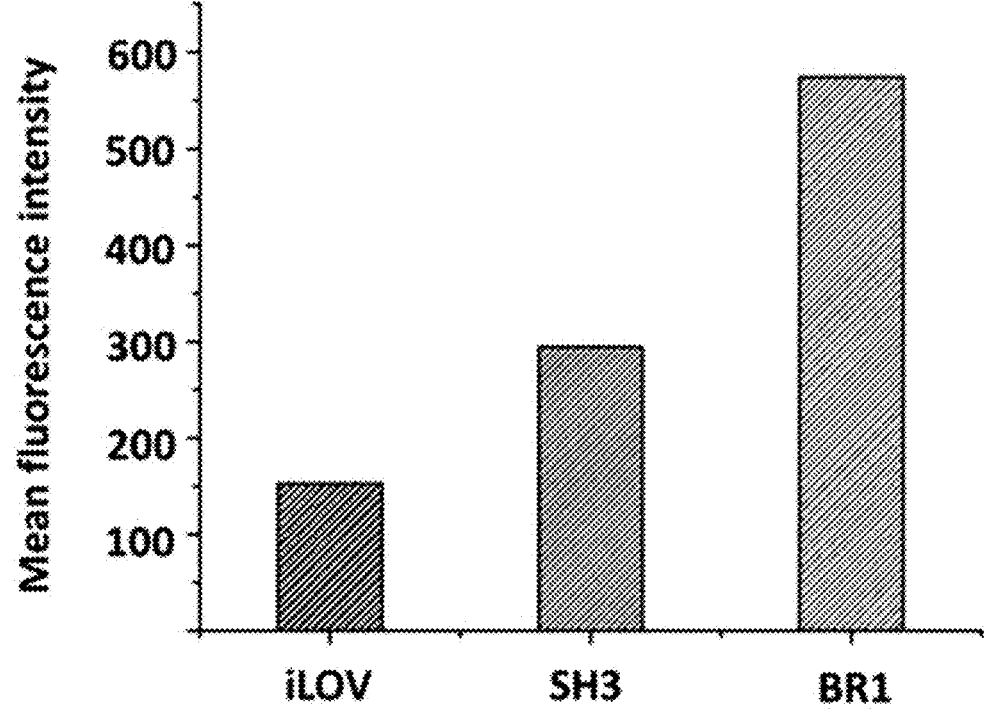
FIG. 4 shows the FACS fluorescence intensities of SH3 and BR1 selected from iLOV initial and final libraries.
FIG. 5 shows the sites of iLOV variants into which mutations were introduced.

A determination was made as to whether groups with improved fluorescence intensity were obtained from the primary and secondary iLOV libraries after 4 rounds of sorting and resorting (FIGS. 2 and 3). Individual clones in the sorted groups were analyzed and iLOV variants with high fluorescence intensity were identified based on fluorescence signals measured by flow cytometry. Two iLOV variants (SH3 and BR1) exhibiting higher fluorescence intensities than iLOV were selected FIGS. 4 and 5).

<Example 4> Analysis of Emission Patterns of the Selected iLOV Variants

Figures 6, 7:
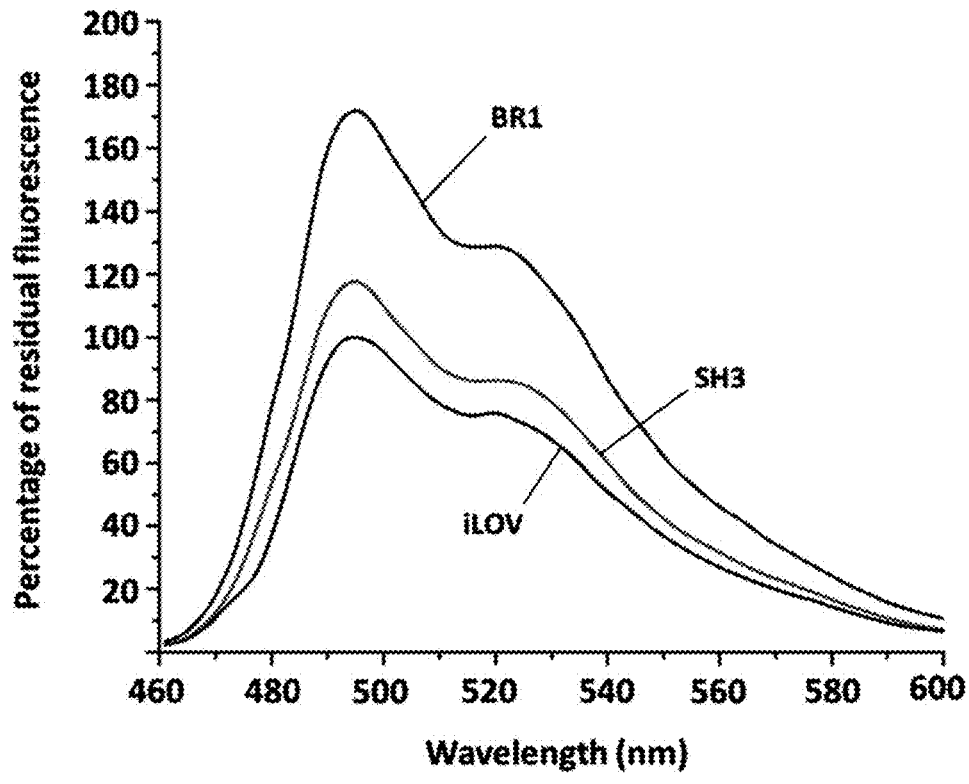
FIG. 6 shows patterns of fluorescence emitted by SH3 and BR1.
FIG. 7 shows the quantum yields of SH3 and BR1.

The emission patterns of the iLOV variants were investigated. Electrons were excited at a wavelength of 450 nm in each purified protein (3 μm) and the resulting emission wavelengths was measured between 470 and 600 nm. As a result, two peaks were observed at 495 nm and 520 nm. The overall fluorescence patterns of iLOV and its variants were similar. The emission intensities of SH3 and BR1 were improved by 20% and 70%, respectively (FIG. 6).

<Example 5> Analysis of Quantum Yields of the iLOV Variants

Quantum yield is defined as the ratio of the number of photons or photoelectrons emitted to the number of photons absorbed upon absorption of light and subsequent emission of photons or photoelectrons. That is, a higher quantum yield indicates a higher conversion of absorbed photons into re-emitted photons. Consequently, a protein with a high quantum yield indicates a bright fluorescence protein. A fluorescent protein with a high quantum yield can be measured to be relatively highly fluorescent even when used in a small amount, which leads to increased sensitivity. The quantum yields of the iLOV variants were determined using fluorescein as a reference. The quantum yields of SH3 and BR1 were 0.40 and 0.45, respectively, which were improved relative to that of wild-type iLOV (0.37) (FIG. 7).

<Example 6> Analysis of Thermostability of the iLOV Variants

Figure 8:
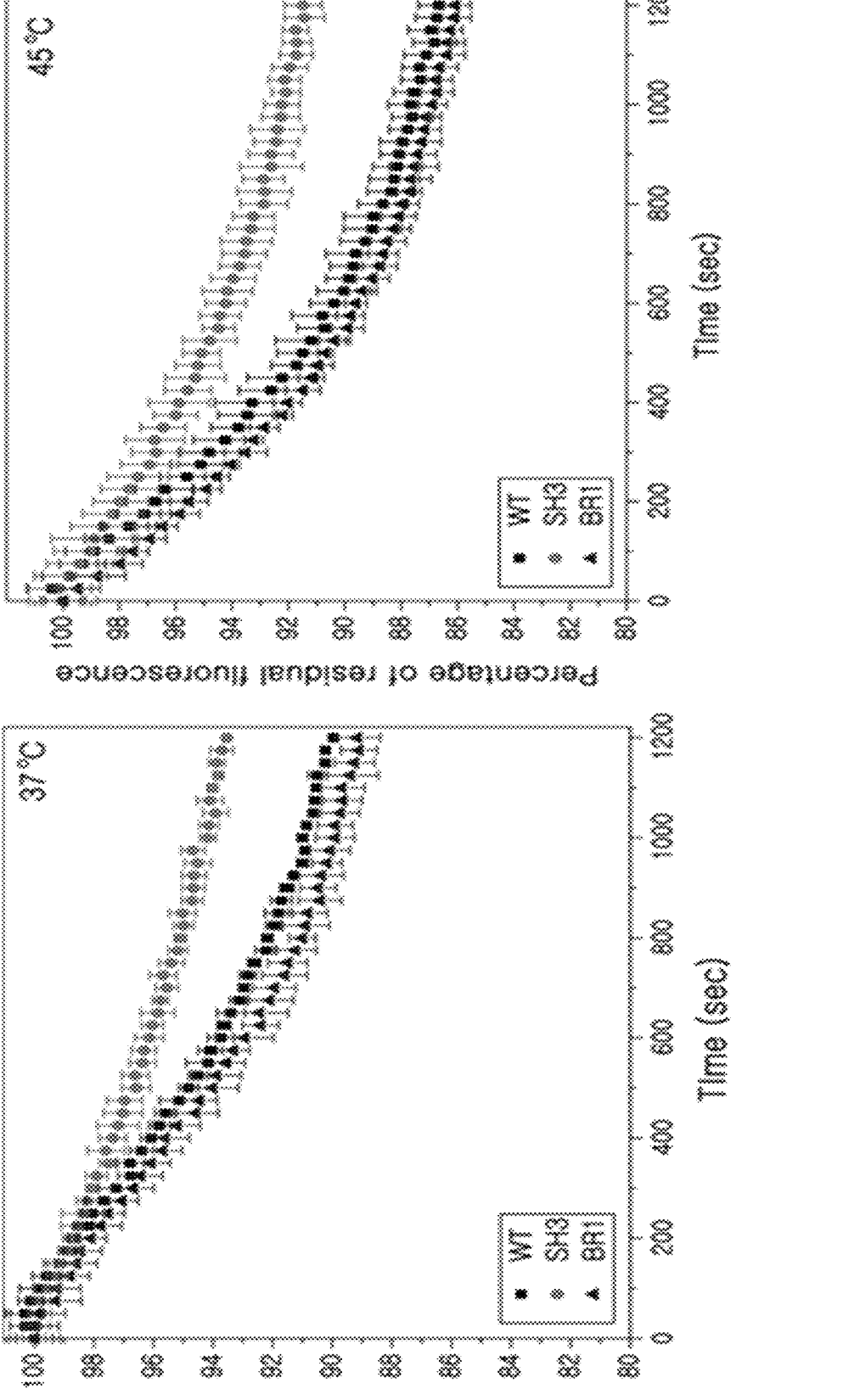
FIG. 8 shows the analysis of thermostability for SH3 and BR1.
Figure 9:
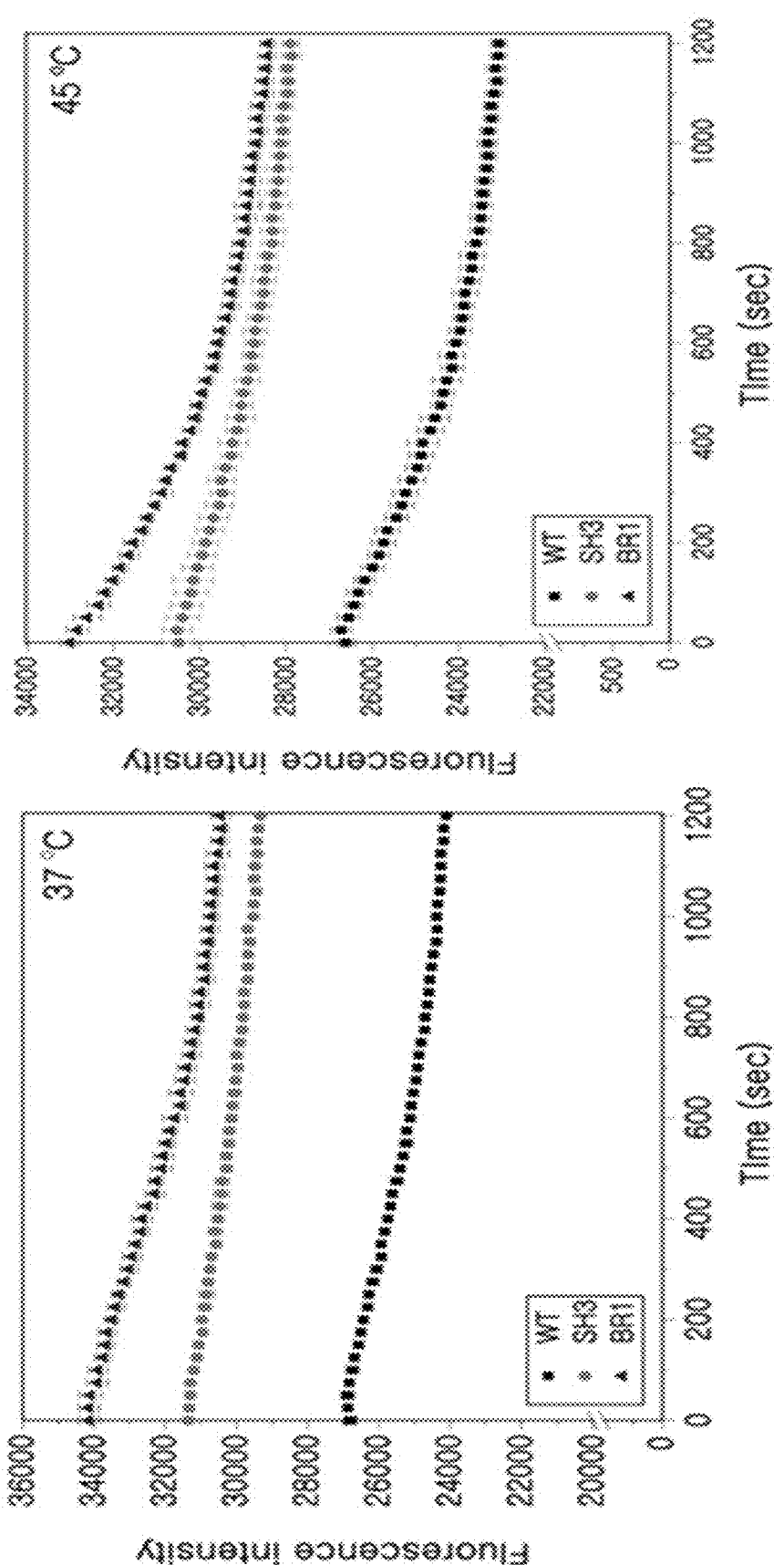
FIG. 9 shows the actual fluorescence intensities in the analysis of thermostability for SH3 and BR1.
Figure 10:
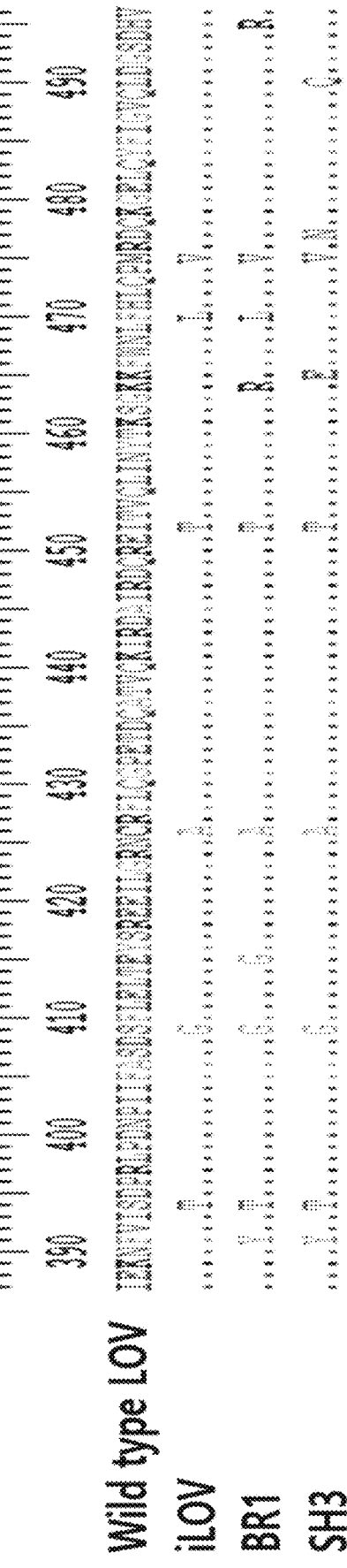
FIG. 10 compares the amino acid sequences of iLOV variants, iLOV, and wild-type LOV.

The thermostabilities of the sorted iLOV variants were measured. To this end, a thermostability experiment was conducted by the following procedure. First, a sample was taken at a predetermined time after exposure of each protein (3 μM) to 37° C. or 45° C. and the brightness of the remaining fluorescent protein was measured. Since the brightness of the fluorescent proteins was affected by temperature, the fluorescence brightness of the sample was measured in a cuvette at a fixed temperature (25° C.) in all measurements after incubation in a thermostat at 25° C. for 30 sec. At this time, the sample was excited at a wavelength of 450 nm and the emission was measured at 495 nm. SH3 showed improved thermal stability and BR1 showed poor thermal stability compared to iLOV (FIG. 8). However, the fluorescence intensity of BR1 was still high (FIG. 9).

Figure 11:
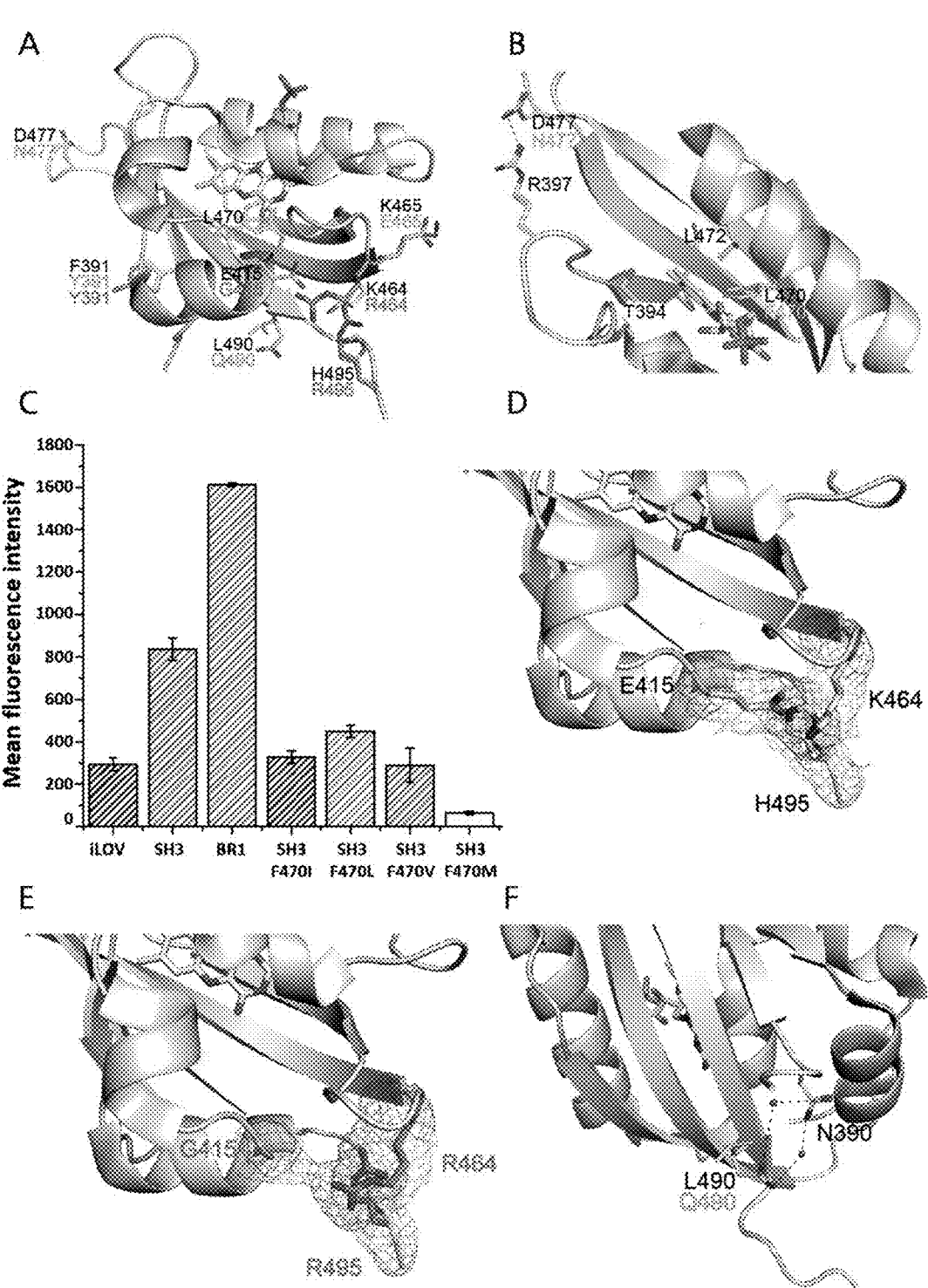
FIG. 11 shows the results of structural interpretation for enhanced spectral properties of SH3 and BR1 via homology modeling analysis.

<Example 7> Structural Interpretation for
Enhanced Spectral Properties of SH3 and BR1 Via
Homology Modeling Analysis SH3 and BR1, respectively, contain five additional mutations (F391Y, K465E, L470F, D477N, and L490Q) and four
additional mutations (F391Y, E415G, K464R, and H495R)
compared to the sequence of iLOV (A of FIG. 11). Phe-470
in SH3 (Lue-470 in iLOV) is conserved in wild-type LOV.
A previous study showed that an F470L substitution of
iLOV improved the fluorescence intensity by triggering
flipping of the Leu-472 toward the FMN isoalloxazine ring.
In the wild-type LOV, the Lue-472 faces away from the
FMN isoalloxazine ring due to the Phe-470. However, the
fluorescence intensity of the SH3 variant was higher than
that of iLOV despite containing the L470F substitution. To
obtain insights into the improving effect of a certain amino
acid substitution at the F470 position of SH3 on fluorescence
intensity, an in silico model was generated using the SWISS-
MODEL. According to the SH3 model, Lue-472 is still
rotated toward the FMN isoalloxazine ring irrespective of
either Phe or Lue at the 470 position (B of FIG. 11), and the
trigger factor for flipping Lue-472 in SH3 might be D477N
substitution. The Asp-477 in iLOV forms a salt bridge with
Arg-397, which increases the binding with FMN. Depletion
of the salt bridge by D477N substitution in SH3 would
enable Lue-472 to flip toward the FMN isoalloxazine ring (B
of FIG. 11). Substitution into smaller hydrophobic residues
(isoleucine, leucine, methionine, and valine) with lower
affinity for the FMN ring than phenylalanine reduced the
fluorescence intensity of SH3, which supports modeling interpretation for Phe-470 of SH3 (C of FIG. 11). The
present inventors, therefore, propose that the increased
structural rigidity of the FMN isoalloxazine ring by L470F
and D477N substitutions contributes to improved fluores-
cence of SH3 over iLOV. Except for the Y391F substitution,
three identified mutations (E415G, K464R, and H495R) of
BR1 are more positively charged residues than those in
iLOV (D and E of FIG. 11). According to the in silico model
for BR1, E415G, K464R, and H495R are located close to the
hydrophilic side of the FMN isoalloxazine ring (E of FIG.
11). A previous study reported that, in an oxidative condi-
tion, LOV protein often loses photostability due to photo-
reduction mediated by semiquinone radicals generated at the
hydrophilic side of the FMN isoalloxazine ring. Based on
the fact that a negatively charged amino acid produces
semiquinone radicals and a proton is involved in converting
a semiquinone radical to hydroquinone, the relatively posi-
tively charged environment of BR1 resulting from three
substitution mutations could reduce the photoreduction by
semiquinone radicals to enhance the fluorescence intensity
of BR1. SH3 showed improved thermostability compared to
wild-type iLOV or BR1. The homology model of SH3
indicates that L490Q substitution can produce water-medi-
ated charge interaction with Asn-390 (F of FIG. 11), which
might be critical for improved thermal stability of SH3.

Although the particulars of the present invention have
been described in detail, it will be obvious to those skilled
in the art that such particulars are merely preferred embodi-
ments and are not intended to limit the scope of the present
invention. Therefore, the substantial scope of the present
invention is defined by the appended claims and their
equivalents.

We claim:

1. A fluorescent composition comprising a flavoprotein improved LOV (iLOV) variant with enhanced florescence intensity compared to iLOV, a nucleic acid molecule encoding the iLOV variant or a vector comprising the nucleic acid molecule, wherein the iLOV variant comprises a portion of the amino acid sequence of the iLOV (SEQ ID NO: 2) and a substitution of the phenylalanine (F) at position 5 in the amino acid sequence of the iLOV (SEQ ID NO: 2) to tyrosine (Y), and wherein the iLOV variant further comprises substitutions of the lysine (K), leucine (L), aspartate (D), and leucine (L) at positions 79, 84, 91, and 104 in the amino acid sequence of the iLOV (SEQ ID NO: 2) to glutamate (E), phenylalanine (F), asparagine (N), and glutamine (Q), respectively.

2. A fluorescent composition comprising a flavoprotein improved LOV (iLOV) variant with enhanced fluorescence intensity compared to iLOV, a nucleic acid molecule encoding the iLOV variant or a vector comprising the nucleic acid molecule, wherein the iLOV variant comprises a portion of the amino acid sequence of the iLOV (SEQ ID NO: 2) and a substitution of the phenylalanine (F) at position 5 in the amino acid sequence of the iLOV (SEQ ID NO: 2) to tyrosine (Y), and wherein the iLOV variant further comprises substitutions of the glutamate (E), lysine (K), and histidine (H) at positions 29, 78, and 109 in the amino acid sequence of the iLOV (SEQ ID NO: 2) to glycine (G), arginine (R), and arginine (R), respectively.

* * * * *